(12) United States Patent
Taguchi et al.

(10) Patent No.: US 8,303,908 B2
(45) Date of Patent: *Nov. 6, 2012

(54) ANALYZING TOOL AND DEVICE

(75) Inventors: Takayuki Taguchi, Kyoto (JP); Shigeru Kitamura, Kyoto (JP); Yuichiro Noda, Kyoto (JP); Toshihiko Harada, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 1826 days.

This patent is subject to a terminal disclaimer.

(21) Appl. No.: 10/533,150

(22) PCT Filed: Oct. 24, 2003

(86) PCT No.: PCT/JP03/13671

§ 371 (c)(1),
(2), (4) Date: Apr. 27, 2005

(87) PCT Pub. No.: WO2004/038425

PCT Pub. Date: May 6, 2004

(65) Prior Publication Data

US 2006/0008381 A1    Jan. 12, 2006

(30) Foreign Application Priority Data

Oct. 28, 2002 (JP) .................................. 2002-312961

(51) Int. Cl.
*B01L 3/00* (2006.01)

(52) U.S. Cl. ............. 422/502; 422/503; 422/64; 422/72

(58) Field of Classification Search .................... 422/100
See application file for complete search history.

(56) References Cited

U.S. PATENT DOCUMENTS

| | | | |
|---|---|---|---|
| 3,864,089 A * | 2/1975 | Tiffany et al. .................. | 494/27 |
| 4,753,776 A | 6/1988 | Hillman et al. | |
| 4,868,129 A | 9/1989 | Gibbons et al. | |
| 5,460,974 A | 10/1995 | Kozak et al. | |
| 6,315,738 B1 | 11/2001 | Nishikawa et al. | |
| 6,383,452 B1 * | 5/2002 | Miyake et al. .................. | 422/63 |
| 6,632,399 B1 | 10/2003 | Kellogg et al. | |
| 2001/0028862 A1 | 10/2001 | Iwata et al. | |
| 2002/0142481 A1 | 10/2002 | Andersson et al. | |
| 2004/0121356 A1 * | 6/2004 | Yamagata et al. ............... | 435/6 |
| 2006/0045799 A1 | 3/2006 | Taguchi | |

FOREIGN PATENT DOCUMENTS

| | | |
|---|---|---|
| EP | 0 698 413 | 2/1996 |
| EP | 0774657 A2 | 5/1997 |
| EP | 0 806 666 | 11/1997 |
| EP | 1 329 717 | 7/2003 |
| JP | 3-59457 | 3/1991 |
| JP | 6-201704 | 7/1994 |
| JP | 8-105901 | 4/1996 |
| JP | 08105901 * | 4/1996 |

(Continued)

*Primary Examiner* — Natalia Levkovich
(74) *Attorney, Agent, or Firm* — Fox Rothschild LLP

(57) ABSTRACT

This invention relates to technology for analyzing a specific component in a sample liquid, and provides an analyzing tool and an analyzing apparatus. Analyzing tool (Y) includes a liquid inlet (61) at a central portion of the tool and a plurality of channels (51) which communicate with liquid inlet (61) and move the sample liquid introduced through liquid inlet (61) by capillary action from the central portion towards a peripheral portion of the tool. Each channel (51) extends linearly for example from the central portion towards the peripheral portion, and the plurality of channels (51) are arranged radially.

10 Claims, 12 Drawing Sheets

FOREIGN PATENT DOCUMENTS

| | | |
|---|---|---|
| JP | 8-114539 | 5/1996 |
| JP | 10-2875 | 1/1998 |
| JP | 10002875 A | 1/1998 |
| JP | 10-501340 | 2/1998 |
| JP | 10-197526 | 7/1998 |
| JP | 10-206417 | 8/1998 |
| JP | 2000-266759 | 9/2000 |
| JP | 2001-50952 | 2/2001 |
| JP | 2002-243726 | 8/2002 |
| JP | 2002-243734 | 8/2002 |
| WO | WO 95/33986 | 12/1995 |
| WO | WO 96/23223 | 8/1996 |
| WO | WO 98/08606 | 3/1998 |

\* cited by examiner

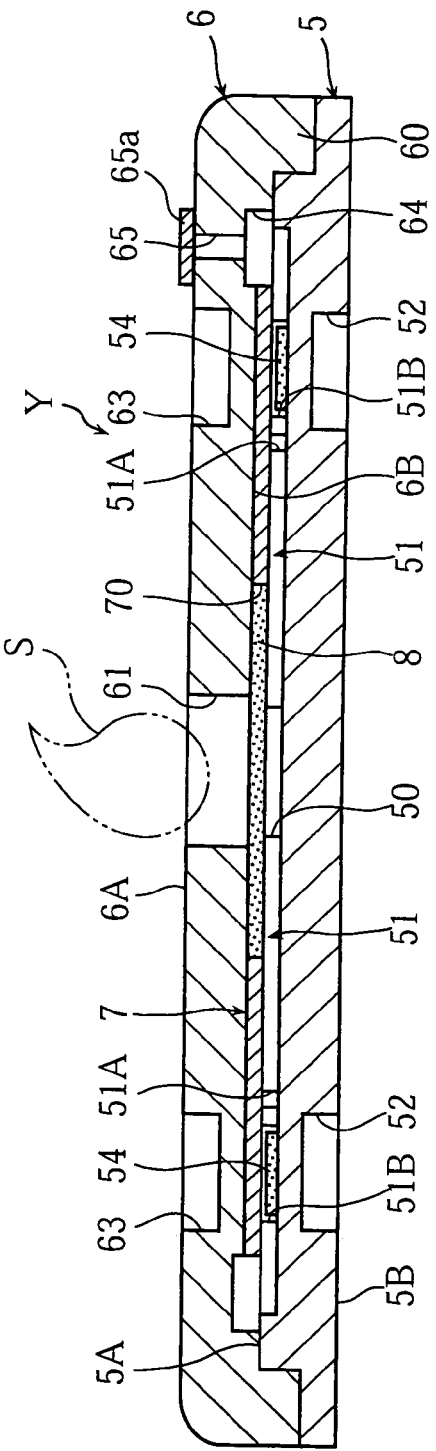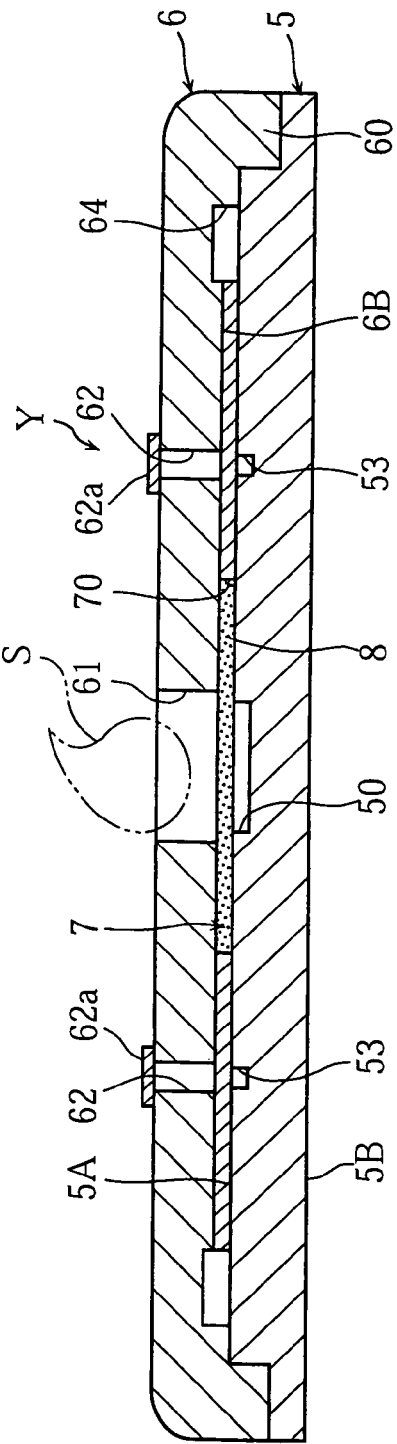

ANALYZING TOOL AND DEVICE

TECHNICAL FIELD

The present invention relates to an analyzing tool and analyzing apparatus used for analyzing a sample liquid.

BACKGROUND ART

Methods of analyzing a sample liquid include for example methods in which a reaction liquid from the reaction of a sample liquid with a reagent is analyzed by optical means. When a sample liquid is analyzed by such means, an analyzing tool is used which provides a place for reaction. Some analyzing tools are equipped with a plurality of channels so that multiple analyses can be performed using one type of sample liquid, or so that multiple types of sample liquid can be subjected to the same analysis.

Analyzing tools equipped with a plurality of channels include those having a rectangular configuration as shown in FIGS. 13A and 13B, in which the main parts of multiple channels 90A and 90B are arranged parallel to one another. On the other hand, there are analyzing tools having multiple channels arranged radially (for example, see JP-A 10-2875 and JP-A 10-501340).

The analyzing tool disclosed in JP-A 10-2875 has a structure wherein a sample liquid is introduced from the outer edge of the analyzing apparatus via capillaries, and an enzyme reaction occurs inside the capillaries.

On the other hand, the analyzing tool disclosed in JP-A 10-501340 has a structure wherein a sample liquid is supplied to multiple channels by means of centrifugal force which is applied to the sample liquid by rotating the analyzing tool.

However, in the analyzing tool 9A shown in FIG. 13A, the operation of supplying the sample liquid is complicated by the fact that the sample liquid needs to be supplied individually to each channel 90A via liquid inlet 91A.

On the other hand, in the analyzing tool 9B shown in FIG. 13B sample liquid can be supplied to multiple channels 90B in one operation because multiple channels 90B are all connected to one liquid inlet 91B. However, as the number of channels 90B increases it becomes difficult to keep the length of channels 90B uniform. Differences in the lengths of channels 90B translate into discrepancies in the length of time it takes for sample liquid to arrive at reaction sites 92B from liquid inlet 91B. As a result, the timing of supply of sample liquid to reaction site 92B is different for each channel 90B, and the amount of time available for the reaction at each reaction site 92B is not uniform. Because this lack of uniformity is reflected in the measurement results, differences in the length of channels 90B ultimately affect measurement accuracy.

Moreover, in order to analyze by optical means sample liquid supplied to channels 90A and 90B, the analyzing tool 9A shown in FIG. 13A and the analyzing tool 9B shown in FIG. 13B require either one photometric system which is scanned or a number of photometric systems corresponding to the number of channels 90A or 90B. This in turn means a more complex photometric system, a larger analyzing apparatus, higher manufacturing costs and higher running costs.

In the analyzing tool described in Japanese Patent Application Laid-open No. H10-2875, because sample liquid need to be supplied individually to each capillary as in the analyzing apparatus 9A shown in FIG. 13A, the operation of supplying the sample liquid is complicated by the necessity for supplying sample liquid as many times as there are capillaries.

By contrast, although in the analyzing tool described in JP-A 10-501340 there is no need to supply sample liquids as many times as there are channels, the analyzing tool must be rotated at high speeds to supply the sample liquid to the channels, generating a rotational force which is directed at the sample liquid. This complicates the device for analyzing sample liquids using the analyzing tool, leading to higher manufacturing costs and also to higher running costs because the analyzing tool needs to be rotated at high speeds.

DISCLOSURE OF THE INVENTION

It is an object of the present invention to allow a sample liquid to be analyzed accurately by means of a simple configuration in which the work of supplying sample liquid to the analyzing tool is reduced while the size of the analyzing apparatus, the manufacturing costs and the running costs are controlled.

An analyzing tool provided by a first aspect of the present invention comprises a liquid inlet provided at a central portion, and a plurality of channels which communicate with the liquid inlet for moving a sample liquid introduced through the liquid inlet by capillary action from the central portion toward a peripheral portion of the tool.

Each channel extends linearly from the central portion towards the peripheral portion for example. In this case, the plurality of channels are preferably arranged radially. The plurality of channels may also be grouped into one or a plurality of collective channels having a common part and individual parts. In this case, the collective channels are preferably formed so as to extend from the central portion while branching towards the peripheral portion of the tool.

The analyzing tool of the present invention is provided for example with a plurality of measurement sites. In this case, it is desirable that each channel be provided with at least one of the plurality of measurement sites, and that the plurality of measurement sites be arranged so as to be on a common circle. In this case, the analyzing apparatus is preferably made in the form of a disk.

It is desirable that two or more of the plurality of channels have reagent parts for reaction with a sample liquid, and that the reagent parts provided at the aforementioned two or more channels may contain different reagents. With this design, it is possible to perform multiple measurements on one type of sample liquid introduced via the liquid inlet.

The analyzing tool of the present invention may further comprise, for example, a substrate and a cover which joins with the substrate. In this case, the liquid inlet may comprise, for example, a through-hole in the substrate or cover, while the plurality of channels may be formed by grooves in the substrate or cover.

The analyzing tool of the present invention may be preferably designed to perform analysis based on tiny quantities of sample liquid. In this case, the principal cross section of the grooves is rectangular with a width of 10-500 μm, a depth of 5-500 μm for example, and a depth/width ratio of $\geqq 0.5$. In the present invention "principal cross section" refers to a cross section perpendicular to the direction of flow of the sample liquid. In the case where the cross-sectional shape is not uniform, the principal cross section refers to a cross section of a part of the channel intended for the flow of the sample liquid.

A second aspect of the present invention provides an analyzing apparatus for performing analysis of a sample liquid using an analyzing tool. The analyzing tool comprises a liquid inlet at a central portion, a plurality of channels which communicate with the liquid inlet and allow a sample liquid introduced through the liquid inlet to flow from the central portion toward a peripheral portion of the tool under capillary action, and a plurality of measurement sites arranged on a common circle. Each of the channels is provided with at least one of the plurality of measurement sites. The analyzing apparatus comprises rotating means for rotating the analyzing tool and detection means for providing a stimulus to the measurement sites and detecting a reaction at the measurement sites. In this analyzing apparatus, stimulus is applied for example as light, and the reactions are detected for example as reflected light, transmitted light or scattered light.

In a preferred embodiment, the plurality of measurement sites are arranged at equal intervals from each other, and the aforementioned rotating means causes the analyzing tool to rotate intermittently at angles corresponding to the intervals between adjacent measurement sites.

BRIEF DESCRIPTION OF THE DRAWINGS

FIG. 5A is a cross-section along line Va-Va in FIG. 3, and FIG. 5B is a cross-section along line Vb-Vb in FIG. 3.

BEST MODE FOR CARRYING OUT THE INVENTION

First to third embodiments of the present invention are explained below with reference to the drawings.

First, the first embodiment of the present invention is explained with reference to FIGS. 1 through 10.

Figure 1:
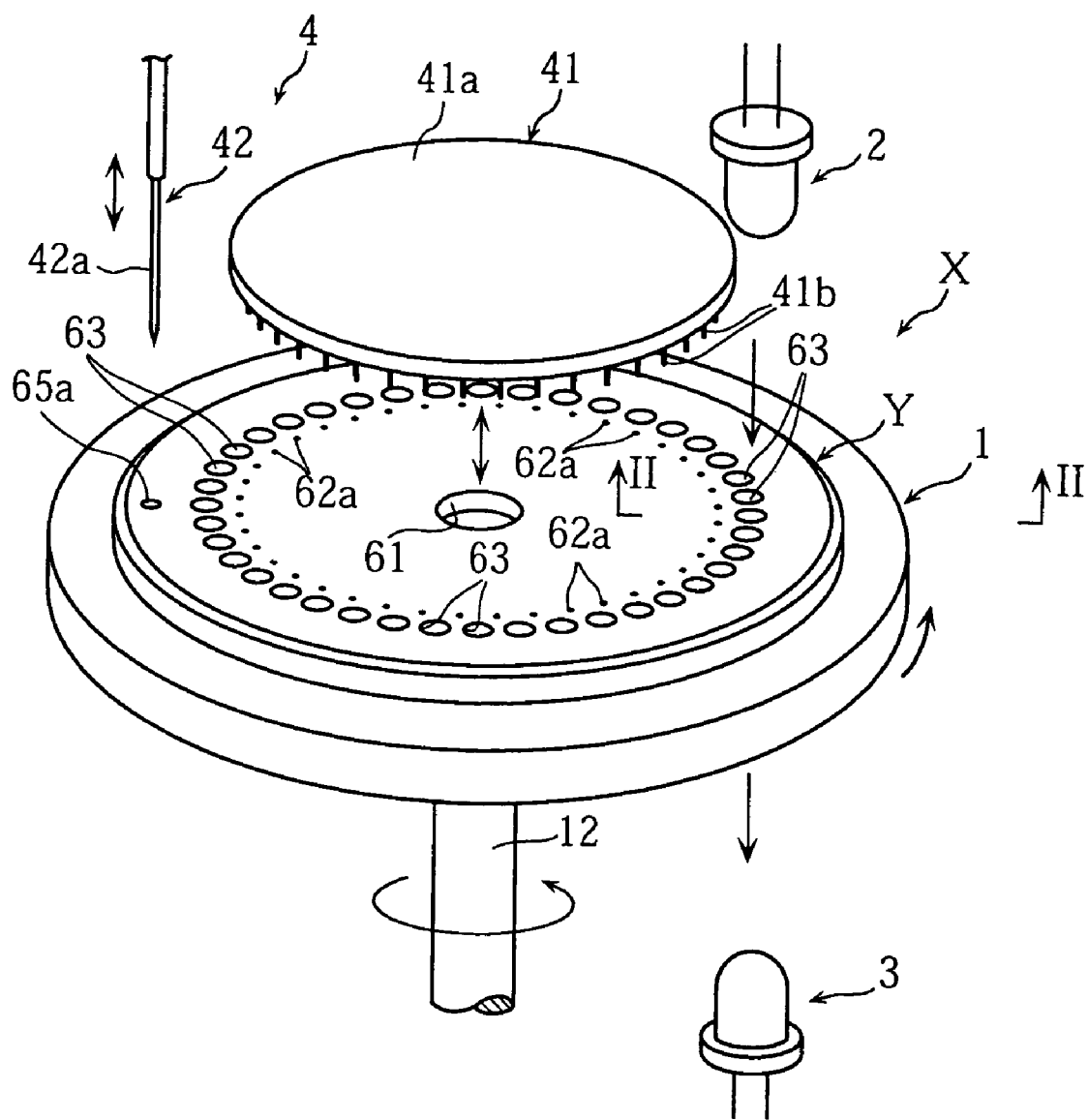
FIG. 1 is a perspective view of a simplified configuration of an analyzing apparatus and analyzing tool according to the first embodiment of the present invention.
Figure 2:
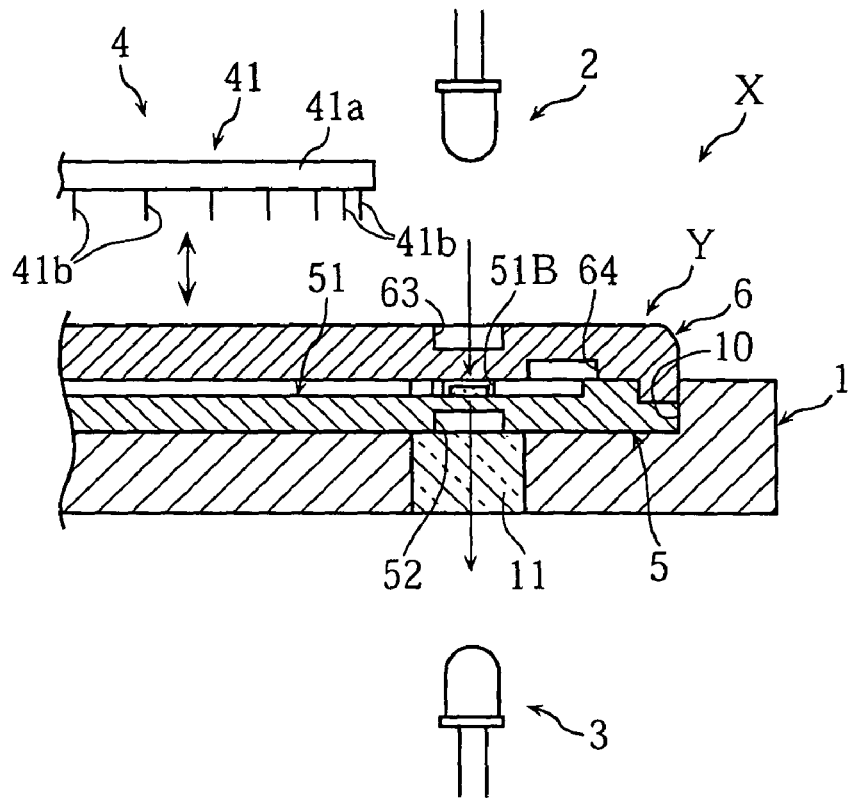
FIG. 2 is a cross-section along line II-II in FIG. 1.

The analyzing apparatus X shown in FIGS. 1 and 2 is equipped with microdevice Y as an analyzing tool for purposes of analyzing a sample liquid, and is provided with mount 1 for mounting microdevice Y, light source 2, light detector 3 and opening mechanism 4.

Figure 3:
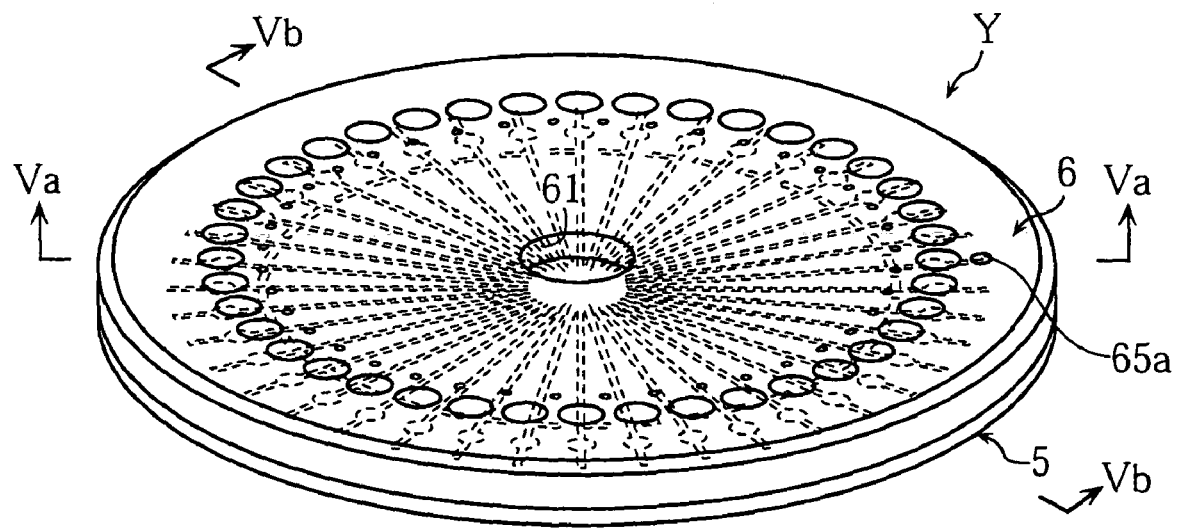
FIG. 3 is a full perspective view of the microdevice shown in FIG. 1.
Figure 4:
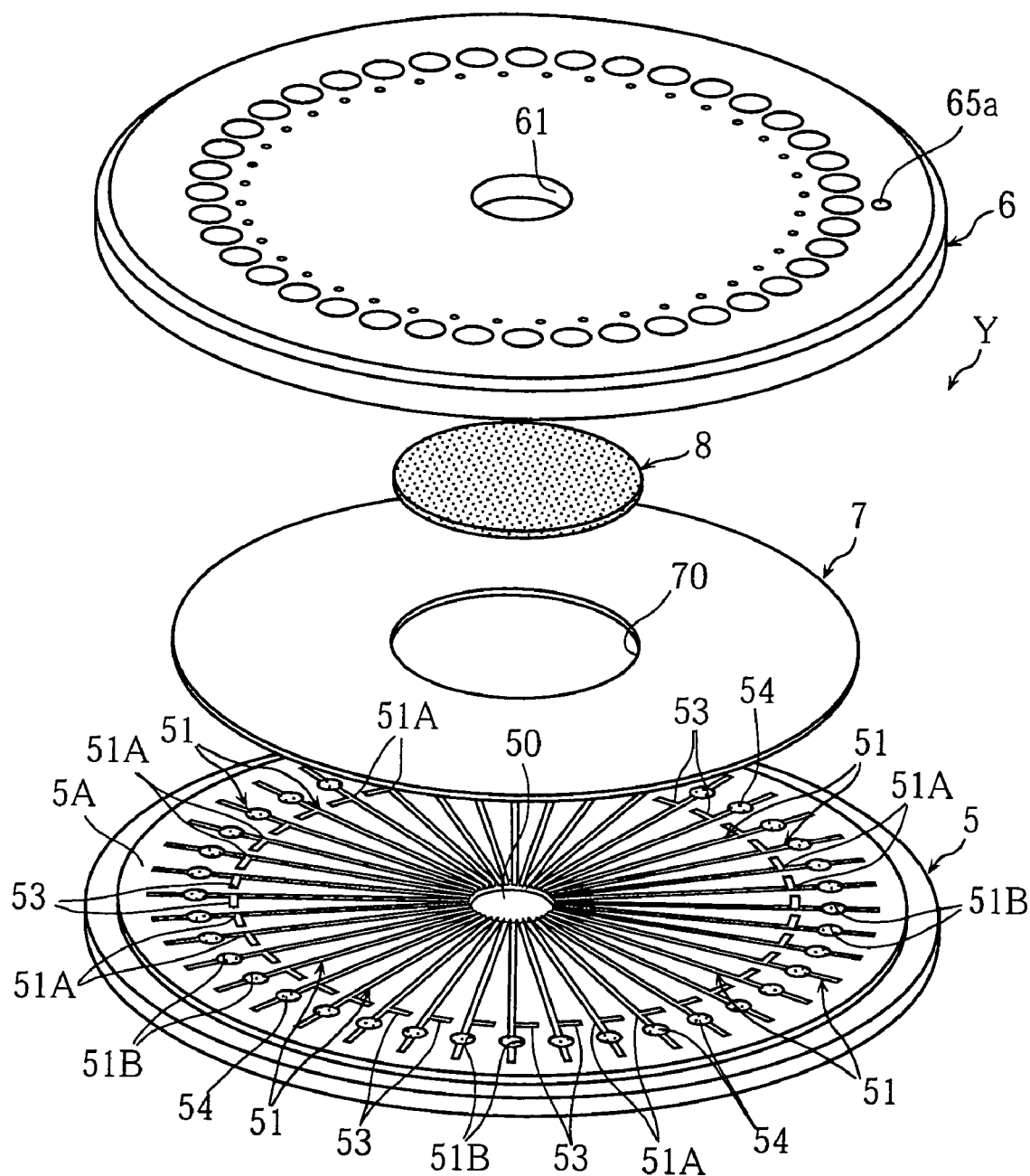
FIG. 4 is an exploded perspective view of the microdevice shown in FIG. 3.

The microdevice Y shown in FIGS. 3 through 5 provides the place for reaction, and has substrate 5, cover 6, adhesive layer 7 and separation membrane 8.

Figure 6:
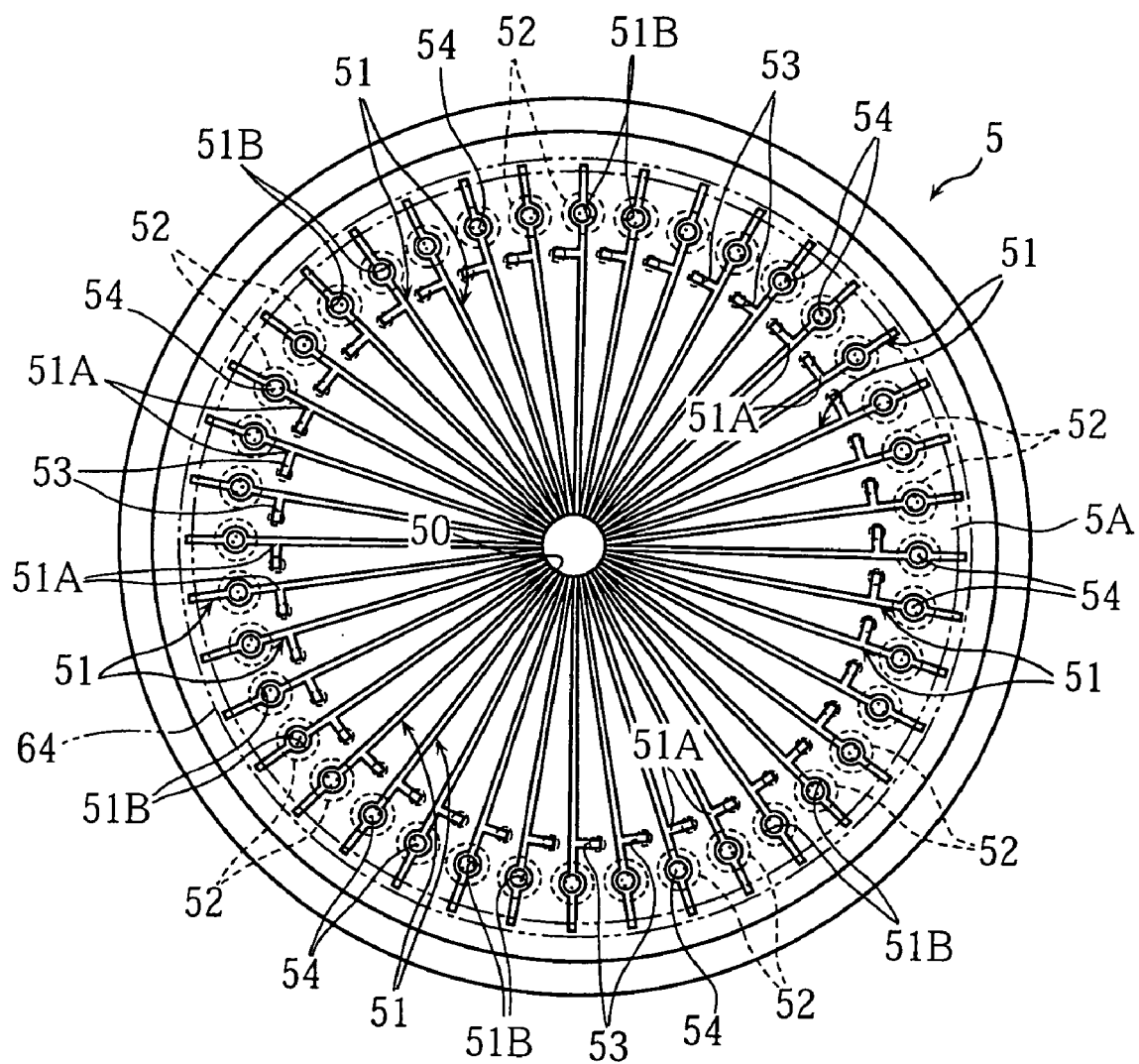
FIG. 6 is a plane view of the substrate of the microdevice shown in FIG. 3.

Substrate 5 is formed as a transparent disk, and has a form in which the outer circumferential edge is stepped down. As shown in FIGS. 5A and 6, substrate 5 has liquid receiver 50 in the central portion, multiple channels 51 which communicate with this liquid receiver 50, multiple grooves 52 and multiple branching channels 53.

Liquid receiver 50 serves the purpose of holding the sample liquid supplied to microdevice Y so that it can be introduced into channels 51. Liquid receiver 50 is formed as a round recess on upper surface 5A of disc 5.

Channels 51 serve the purpose of moving the sample liquid, and are formed on upper surface 5A of substrate 5 so as to communicate with liquid receiver 50. As shown in FIG. 5A, channels 51 are connected to liquid inlet 61 of cover 6 (described below) via liquid receiver 50, and are basically formed linearly extending from the central portion towards the outer edge. As a result, multiple channels 51 have the same channel length and are arranged radially. Each channel 51 has a branch 51A and a reaction site 51B. That part of each channel 51 excluding reaction site 51B has a roughly uniform rectangular cross-section. Channels 51 are formed so that this rectangular cross-section is about 10-500 µm wide and 5-500 µm high, for example, so that the width/height ratio is at least 0.5.

As shown in FIGS. 4 and 6, branching channels 53 which communicate with channels 51 extend from branches 51A. Branches 51A are set as close as possible to reaction sites 51B, so that the distance between branches 51A and reaction sites 51B is as small as possible. Branching channels 53 have a roughly uniform rectangular cross-section, and this rectangular cross-section has dimensions similar to those of the channels.

Reaction sites 51B have a greater cross-sectional area than the main cross-section of channels 51. The individual reaction sites 51B are placed on the same circle. Reaction sites 51B are provided with reagent parts 54 as shown in FIG. 5A. However, reagent parts 54 do not necessarily have to be provided for all channels 51, and the reagent part are omitted for channels which will be used to correct for the effect of color or flavor of the sample liquid.

Reagent parts 54 are in a solid form which dissolves when the sample liquid is supplied, and develops color as it reacts with a specific component in the sample liquid. In this embodiment, multiple types of reagent parts 54 having different components or compositions for example are prepared so that multiple measurements can be performed in microdevice Y.

Multiple recesses 52 are sites for emission of transmitted light to underside 5B of substrate 5 when reaction sites 51B are illuminated with light from upper surface 5A of substrate 5 as described below (see FIGS. 1 and 2). Each recess 52 is located on underside 5B of substrate 5 at a site corresponding to a reaction site 51B. As a result, as shown in FIG. 6, multiple recesses 52 are arranged on the same circle at an outer peripheral portion of substrate 5.

Substrate 5 is formed by resin molding using a transparent resin material such as poly-methyl methacrylate (PMMA) or another acrylic resin or polydimethylsiloxane (PDMS). Liquid receiver so, multiple channels 51, multiple recesses 52 and multiple branching channels 53 can be incorporated at the same time during the aforementioned resin molding by manipulating the form of the mold.

The inner surfaces of liquid receiver 50, multiple channels 51, multiple recesses 52 and multiple-branching channels 53 are preferably given a hydrophilic treatment. A variety of known methods can be adopted for the hydrophilic treatment, and for example it is favorably performed by bringing all the inner surfaces into contact first with a mixed gas containing fluorine gas and oxygen gas and then with water or steam. Because hydrophilic treatment is performed using gas, water and the like in this method, it can be applied reliably even to standing surfaces which are difficult to treat with ultraviolet irradiation, a conventional method of hydrophilic treatment. Hydrophilic treatment of the inner surfaces is performed for example with a contact angle of 0 to 80 degrees with respect to pure water.

Figure 7:
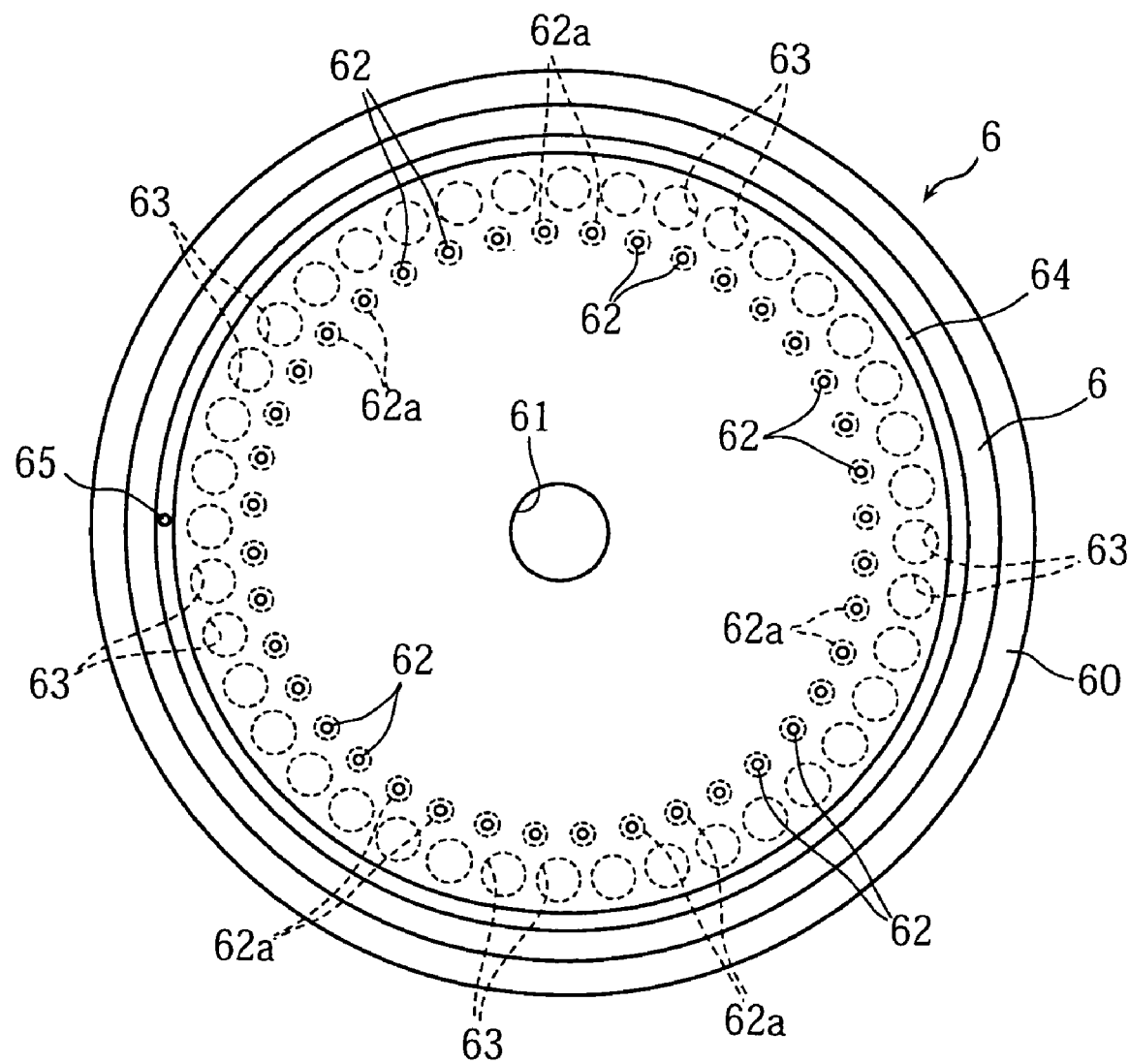
FIG. 7 shows the underside of the cover of the microdevice shown in FIG. 3.

Cover 6 is formed as a disc with the outer circumferential edge overhanging downward. The overhanging part 60 of cover 6 is the part which contacts the stepped edge of substrate 5. As shown in FIGS. 5 and 7, cover 6 has liquid inlet 61, multiple first gas exhaust holes 62, multiple recesses 63, common channel 64 and second gas exhaust hole 65.

Liquid inlet 61 is used when introducing the sample liquid, and is formed as a through-hole. As clearly shown in FIG. 5, liquid inlet 61 is formed in the central portion of cover 6 so as to be located directly above liquid receiver 50 of substrate 5.

First gas exhaust holes 62 are provided for exhausting gas in channels 51, and are formed as through-holes. As shown clearly in FIG. 5B, first gas exhaust holes 62 are formed so as to be located directly above branching channels 53 of substrate 5. As a result, multiple first gas exhaust holes 62 are located on the same circle as shown in FIGS. 4 and 7. As clearly seen in FIG. 5B, the top opening of each first gas exhaust hole 62 is closed by a seal 62a. Seals 62a can be formed from aluminum or another metal or from resin. Seals 62a are fixed to substrate 5 by means of an adhesive for example, or by fusion.

Multiple recesses 63 are sites for illuminating reaction sites 51B with light from the top surface 6A of cover 6 as described below (see FIGS. 1 and 2). As shown in FIG. 5A, each recess 63 is positioned on the upper surface 6A of cover 6 so as to be located directly above a reaction site 51B. As a result, as shown in FIGS. 4 and 7, multiple recesses 63 are arranged on the same circle at an outer peripheral portion of cover 6.

Common channel 64 is a channel for conducting gas to second gas exhaust hole 65 when gas inside channels 51 is exhausted to the outside. As shown in FIGS. 5 and 7, common channel 64 is formed as a ring-shaped groove at an outer peripheral portion on underside 6B of cover 6. As shown in FIGS. 5A and 6, common channel 64 communicates with multiple channels 51 of substrate 5.

Second gas exhaust hole 65 is formed as a through-hole communicating with common channel 64, as shown in FIGS. 5A and 7. The top opening of second gas exhaust hole 65 is closed by seal 65a. Seal 65a may be similar to the seals 62a used to close first gas exhaust holes 62.

Cover 6 can be formed by resin molding using a transparent resin material in the same way as substrate 5. Liquid inlet 61, multiple first gas exhaust holes 62, multiple recesses 63, common channel 64 and second gas exhaust hole 65 can be incorporated at the same time during the aforementioned resin molding. It is also desirable that at least that part of cover 6 facing channels 51 of substrate 5 be given a hydrophilic treatment. The methods adopted for hydrophilic treatment can be similar to those used for hydrophilic treatment of substrate 5.

As clearly shown in FIG. 5, adhesive layer 7 serves the purpose of joining cover 6 to substrate 5. As shown in FIGS. 4 and 5, adhesive layer 7 is formed by placing an adhesive sheet having through-hole 70 in the central portion between substrate 5 and cover 6. The diameter of through-hole 70 of adhesive layer 7 is made larger than the diameters of liquid receiver 50 of substrate 5 and liquid inlet 61 of cover 6. A sheet of a substrate material both surfaces of which have been made adhesive can be used as the adhesive sheet.

Separation membrane 8 serves to separate the solid component of the sample liquid, such as the blood cell component in blood. As shown in FIG. 5, separation membrane 8 has a diameter corresponding to the diameter of through-hole 70 in adhesive layer 7, and is placed between liquid receiver 50 of substrate 5 and liquid inlet 61 of cover 6 so as to fit into through-hole 70 of adhesive layer 7. Because liquid receiver 50 is formed as a recess, there is a gap between separation membrane 8 and the bottom of liquid receiver 50. Because the diameter of separation membrane 8 corresponds to the diameter of through-hole 70, which is larger than that of liquid receiver 50, that part of each channel 51 closest to liquid receiver 50 is covered by separation membrane 8. Arranging separation membrane 8 in this way allows sample liquid introduced through liquid inlet 61 to reach liquid receiver 50 after passing through the thickness of separation membrane 8.

A porous body for example can be used as separation membrane 8. Porous bodies which can be used as separation membrane 8 include for example papers, foams, woven fabrics, nonwoven fabrics, knits, membrane filters, glass filters and gels. When blood is used as the sample liquid and the blood cell component is separated from blood by separation membrane 8, it is desirable that a body with a pore size of 0.1 to 10 μm be used as separation membrane 8.

Mount 1 of the analyzing apparatus X shown in FIGS. 1 and 2 has recess 10 for holding microdevice Y. Light-transmitting region 11 is set in mount 1. This light-transmitting region 11 is provided at a site corresponding to reaction sites 51B when microdevice Y is mounted in recess 10. This light-transmitting region 11 is formed by composing the target site of mount 1 from a transparent material such as transparent resin. Of course, all of mount 1 can also be formed of a transparent material. Mount 1 is supported by rotating shaft 12, in a configuration wherein mount 1 rotates when rotating shaft 12 is rotated. Rotating shaft 12 is connected to a drive mechanism (not shown), and is controlled so as to rotate at angles corresponding to the spacing of reaction sites 51B on microdevice Y.

Light source 2 illuminates reaction sites 51B of microdevice Y, and is fixed in a position which can face recesses 63 of cover 6. Light source 2 is composed for example from a mercury lamp or white LED. When using these light sources, light from light source 2 is sent through a filter before illuminating reaction sites 51B, although this is not shown in the figures. This is so that light of a wavelength conforming to the light absorption characteristics of the component to be analyzed in the reaction liquid will be selected by the filter.

Light detector 3 receives light passing through reaction sites 51B, and is fixed in a position which can face recesses 52 of substrate 5 on the same axis as light source 2. The amount of light received by this light detector 3 is the basis for analyzing (by computing concentration for example) the sample liquid. Light detector 3 is formed by a photo diode for example.

Opening mechanism 4 has first opening-forming element 41 for forming openings in seal 62a, and second opening-forming element 42 for forming an opening in seal 65a. These opening-forming elements 41 and 42 can be moved up and down repeatedly by means of an actuator (not shown).

Figure 8:
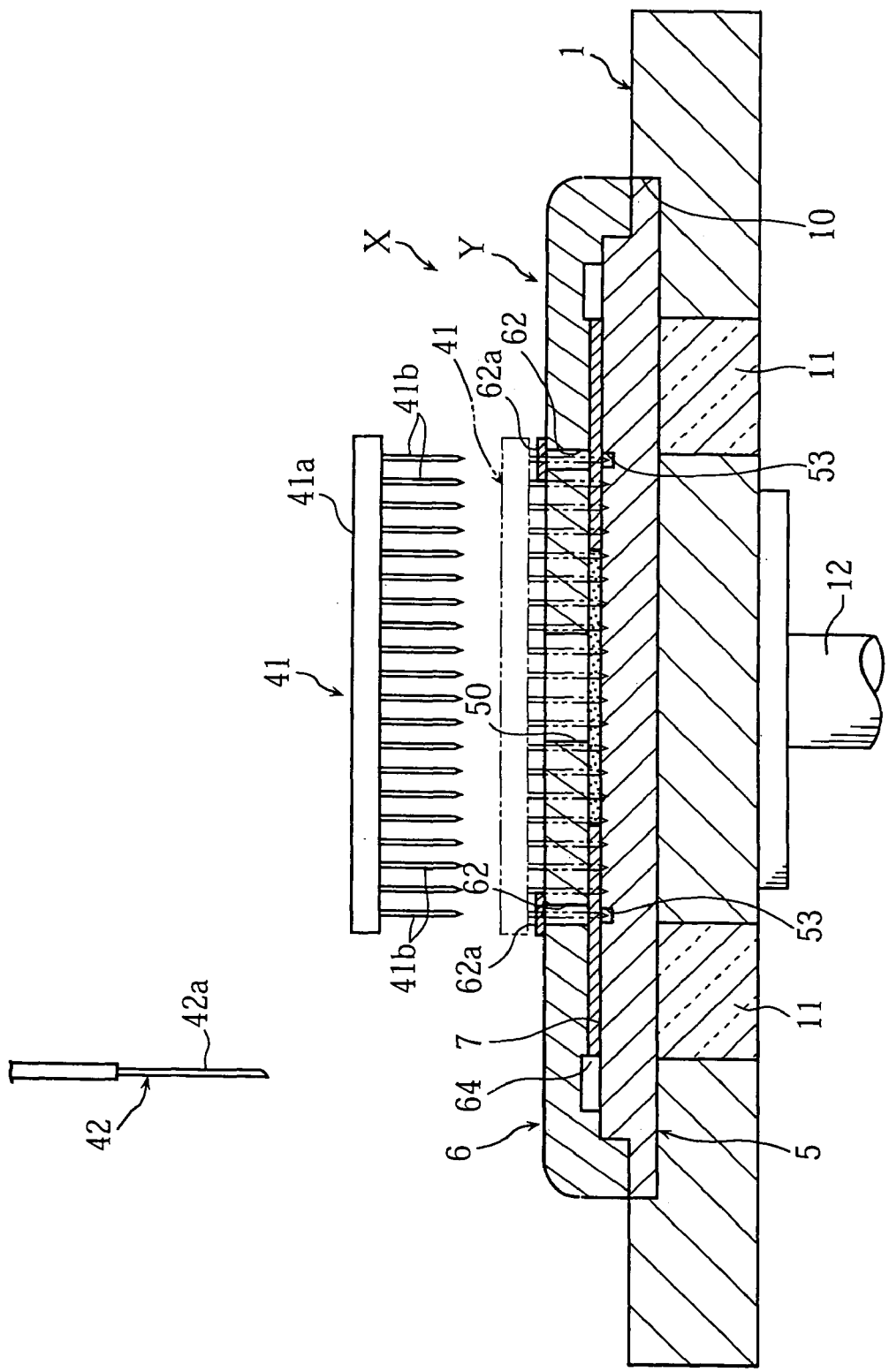
FIG. 8 is a cross-section for explaining the operation of opening the first gas exhaust holes of the microdevice shown in FIG. 3.

First opening-forming elements 41 have multiple needles 41b protruding downwards from the underside of disk-shaped substrate 41a. As shown in FIG. 8, the diameter of needles 41b is smaller than that of first gas exhaust holes 62 in cover 6. Each individual needle 41b corresponds to the position of a first gas exhaust hole 62, and all are arranged on a single circle. Consequently, if first opening-forming element 41 is moved downwards with needles 41b of first opening-forming element 41 aligned with first gas exhaust holes 62 of cover 2, openings can be formed all at once in multiple seals 62a. In this way, first gas exhaust holes 62 are opened and the interiors of channels 51 are made to communicate with the outside via branching channels 53 and first gas exhaust holes 62.

Figure 9:
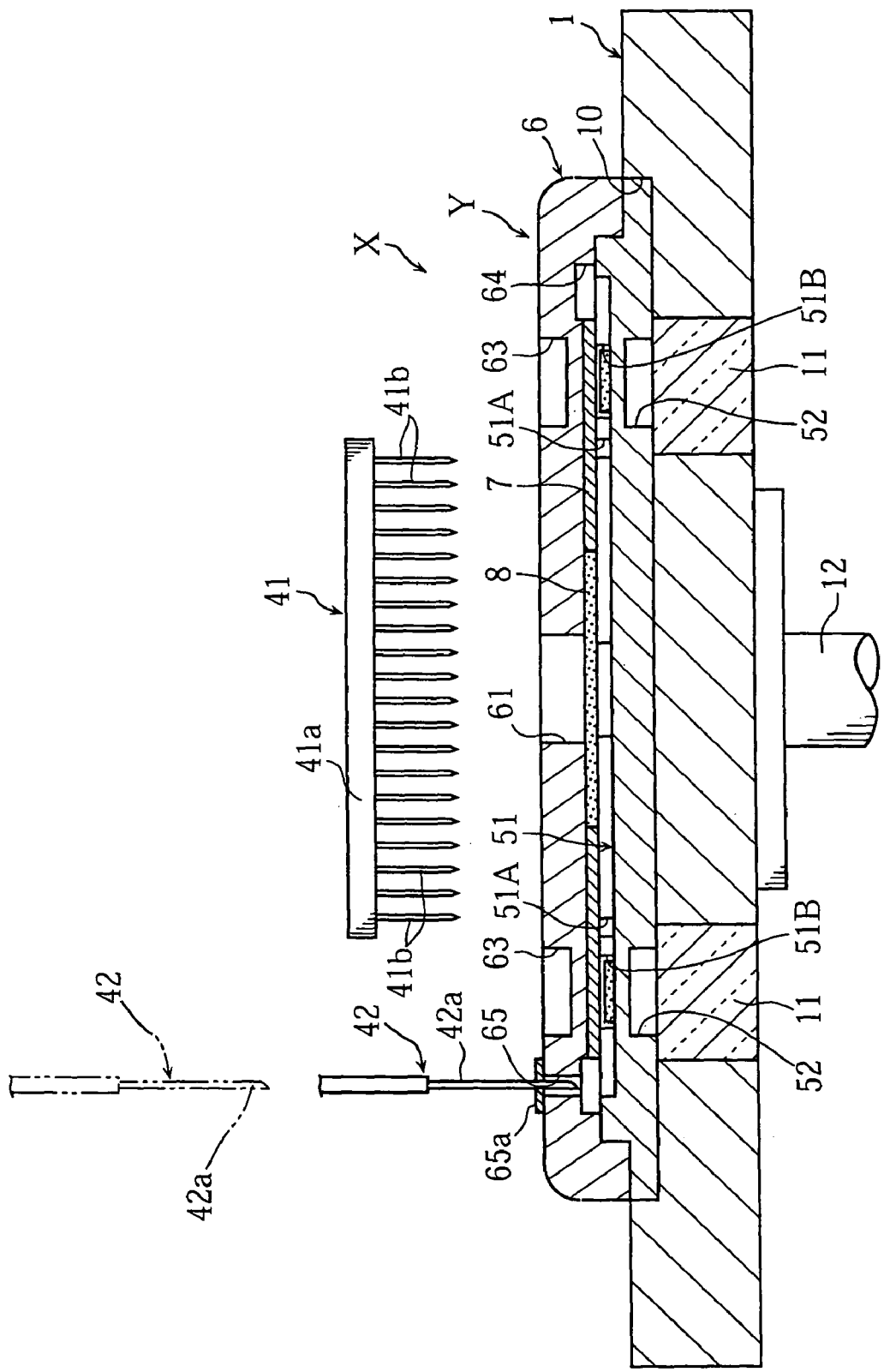
FIG. 9 is a cross-section for explaining the operation of opening the second gas exhaust hole of the microdevice shown in FIG. 3.

Second opening-forming element 42 has needle 42a as shown in FIGS. 1 and 9. The diameter of needle 42a is made smaller than the diameter of second gas exhaust hole 65 in cover 6. Consequently, if second opening-forming element 42 is moved downward with needle 42a of second opening-forming element 42 aligned with second gas exhaust hole 65 of cover 6, an opening can be formed in seal 65a. In this way, second gas exhaust hole 65 is opened and the interior of channels 51 are made to communicate with the outside via common channel 64 and second gas exhaust hole 65.

Of course, the method of opening first and second gas exhaust holes 62 and 65 is not limited by the example described above. For example, first and second gas exhaust holes 62 and 65 can also be opened by applying energy to sheets 62a and 65a to melt or deform sheets 62a and 65a. A light source such as a laser, an ultrasound transmitter, a heater or the like can be used to apply energy. Of course, gas exhaust holes 62 and 65 can also be opened by peeling off sheets 62a and 65a.

When analyzing a sample liquid, as shown in FIG. 5, it is necessary to supply sample liquid S to microdevice Y via sample inlet 61. Sample liquid S is supplied for example by dripping sample liquid S into liquid inlet 61. Sample S can be supplied in this way with microdevice Y mounted on analyzing apparatus X, but it is preferable to mount microdevice Y on analyzing apparatus X after sample liquid S has already been supplied to microdevice Y.

When sample liquid S has been supplied to microdevice Y, sample S arrives at liquid receiver 50 after passing through separation membrane 8 in the direction of thickness, as can be predicted from FIG. 5. At this time, the solid component is removed from sample liquid S. If blood is used as the sample liquid for example, the blood cell component is removed from the blood. Since first and second gas exhaust holes 62 and 65 are closed while sample liquid S is being supplied, sample liquid S is held in liquid receiver 50 and is not conducted in channels 51A, as shown in a typical view in FIG. 10A.

This embodiment is configured so that the sample liquid moves in the direction of thickness of separation membrane 8 and the solid component is removed. Consequently, the retention time of the sample liquid in separation membrane 8 is shorter than it would be if the solid component were removed by moving the sample liquid in the plane direction of separation membrane 8. As a result, less time is required to remove the solid component.

To conduct sample liquid S through channels 51, openings can be formed simultaneously in multiple seals 62a. As shown in FIG. 8, formation of openings in multiple seals 62a can be accomplished by first moving first opening-forming element 41 downward to push needles 41b through seals 62a, and then moving first opening-forming element upward to remove needles 41b from seals 62a. In this way, openings are formed simultaneously in multiple seals 62a. The downward and upward movement of first opening-forming element 41 is performed automatically in analyzing apparatus X by for example by the operation of an operating switch by a user.

Once openings have been formed in seals 62a, the interiors of channels 51 communicate via first gas exhaust holes 62 and branching channels 53. Consequently, the sample liquid S held in liquid receiver 50 moves through the interior of channels 51 by capillary action. As shown by the arrows in FIG. 10A, when sample liquid S reaches branches 51A it is unable to pass branches 51A to reach reaction sites 51B, and is introduced into branching channels 53. In this way, as shown in a typical view in FIG. 10B, a condition is achieved in which sample liquid S is present very near reaction sites 51B, and preparation is complete for reaction of sample liquid S with reagents in reaction sites 51B.

In order to supply sample liquid S to reaction sites 51B it is sufficient to form an opening in seal 65a. As shown in FIG. 9, formation of an opening in seal 65a is accomplished by first moving second opening-forming element 42 down to push needle 42a into seal 65a, and then moving second opening-forming element 42 to remove needle 42a from seal 65a. Downward and upward movement of second opening-forming element 42 is accomplished automatically in analyzing apparatus X by operation of an operating switch by a user for example.

Figure 10A:
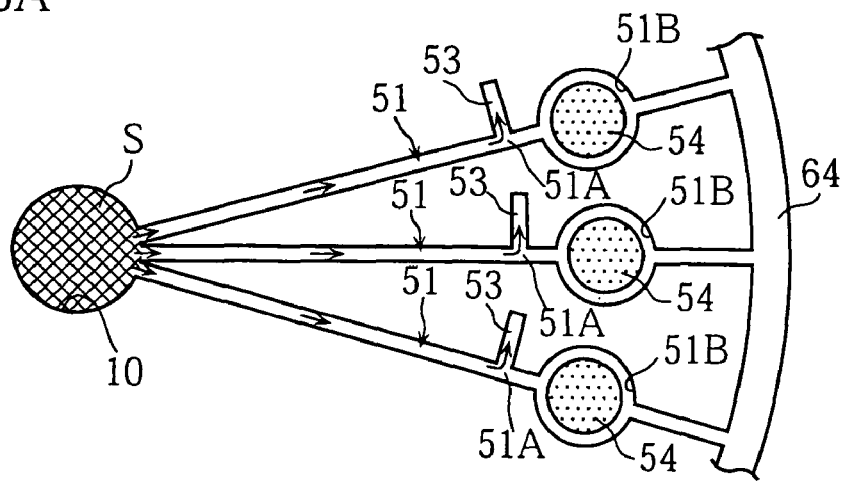
FIGS. 10A through 10C are typical views for explaining the movement of sample liquid in the channels of the microdevice shown in FIG. 3.
Figure 10B:
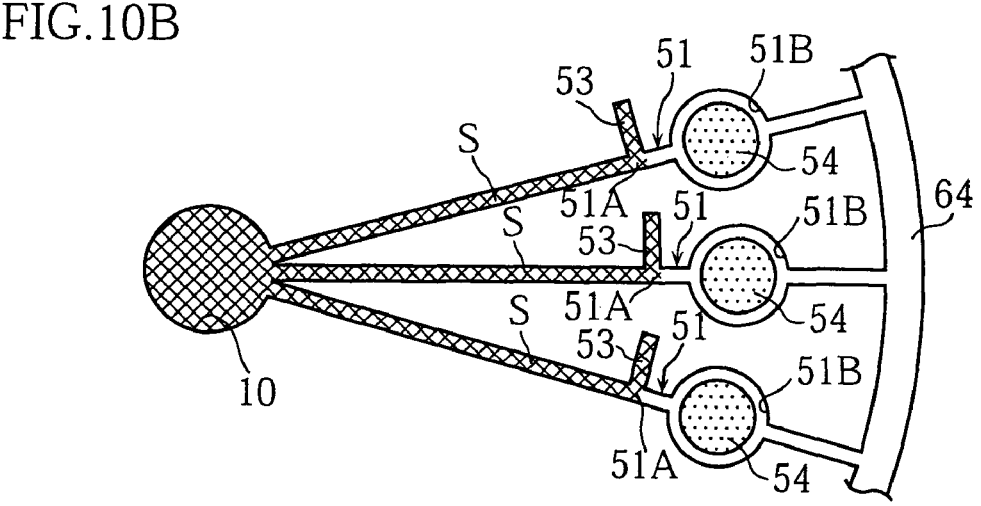
Figure 10C:
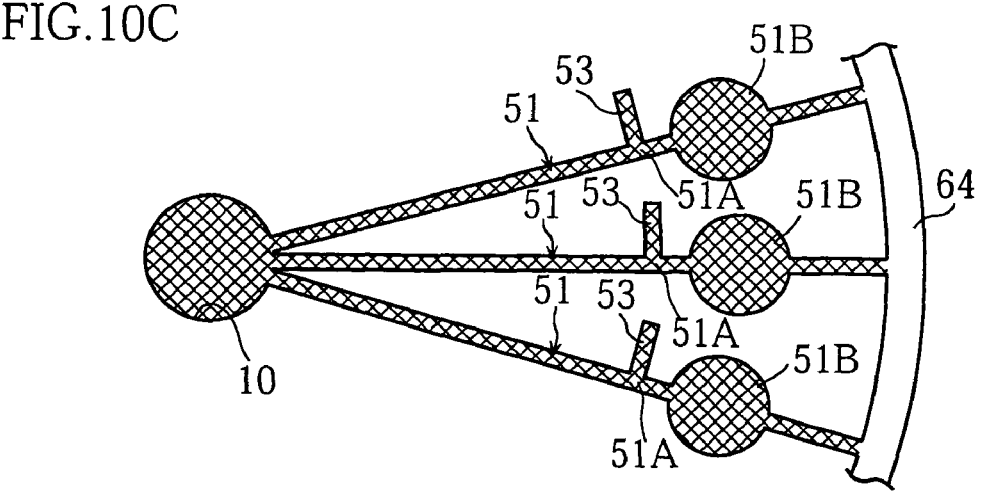

When a hole has been formed in seal 65a, the interiors of channels 51 communicate via second gas exhaust hole 65 and common channel 64. Consequently sample liquid S, the movement of which had been stopped just before reaction sites 51B, moves again through channels 51 by capillary action. In this way, in each channel 51 sample liquid S moves beyond branches 51A as shown in FIG. 10C and is supplied all at once to multiple reaction sites 51B.

In reaction sites 51B, reagent 54 is dissolved by the sample liquid and a liquid phase reaction system is formed. In this way, sample liquid S reacts with the reagent, and for example the liquid phase reaction system exhibits coloration correlating with the amount of the component to be detected in the sample, or a reaction product is produced corresponding to the amount of the component to be detected. As a result, the liquid phase reaction system of reaction sites 51B exhibits translucency (light absorbency) according to the amount of the component to be detected. A fixed time after a sample is supplied to reaction sites 51B, reaction sites 51B are illuminated with light from light source 2 as shown in FIGS. 1 and 2, and the amount of transmitted light at that time is measured at light detector 3. Illumination from light source 2 and reception of transmitted light at receptor 3 are performed for all reaction sites 51B set in channels 51 as mount 1 is rotated successively at fixed angles. Analyzing apparatus X analyzes the sample substrated on the amount of light received at light detector 3, for example by computing concentration of the component to be detected.

In the analysis technique explained above, sample liquid S is first conducted near reaction sites 51B (to branches 51A), after which seal 65a is opened to supply sample liquid S from branches 51A to reaction sites 51B. That is, by opening just one gas exhaust hole it is possible to supply sample liquid S to reaction sites 51B in multiple channels 51. Consequently, the time taken from initiation of the supply operation (opening of seal 65a) of sample liquid S until sample S is supplied to reaction sites 51B is shortened, and there is less variation in time taken from initiation of supply for each channel 51 or even for each measurement (each analyzing tool) until the sample is supplied. In other words, it is possible to suitably control the reaction initiation timing in reaction sites 51B by the operation of opening seal 65a.

In microdevice Y, because liquid inlet 61 is connected to multiple channels 51, supply of sample liquid to multiple channels 51 can be accomplished all at once by a single dripping operation. As a result, in microdevice Y supply of sample liquid is less complicated than it is when sample liquid is supplied individually to each channel 51.

In analyzing apparatus X, illumination and reception of transmitted light from reaction sites 51B is accomplished by rotating microdevice Y at a fixed pitch. As a result, only one fixed pair of light source 2 and light detector 3 is required for the measurement system, simplifying the structure of analyzing apparatus X and allowing the size of analyzing apparatus X, the manufacturing costs and the running costs required for light measurement to be controlled. Because analyzing apparatus X is configured so that microdevice Y is rotated at a fixed pitch, there is no need for high-speed rotation as when centrifugal force is applied. As a result, the power required to rotate microdevice Y can be small, and the power source for rotating mount 1 (microdevice Y) can be one with a relatively low output. In this way, it is possible to simplify the mounting configuration of analyzing apparatus X and also control the size of analyzing apparatus X, the manufacturing costs and the running costs required for light measurement.

Next, microdevices according to the second and third embodiments of the present invention are explained. However, in the figures used in the following explanation the channels and other parts for moving gasses and liquids are shown in typical view, the same symbols are used for the same elements as in microdevice Y in the first embodiment, and redundant explanations are omitted.

Figure 11:
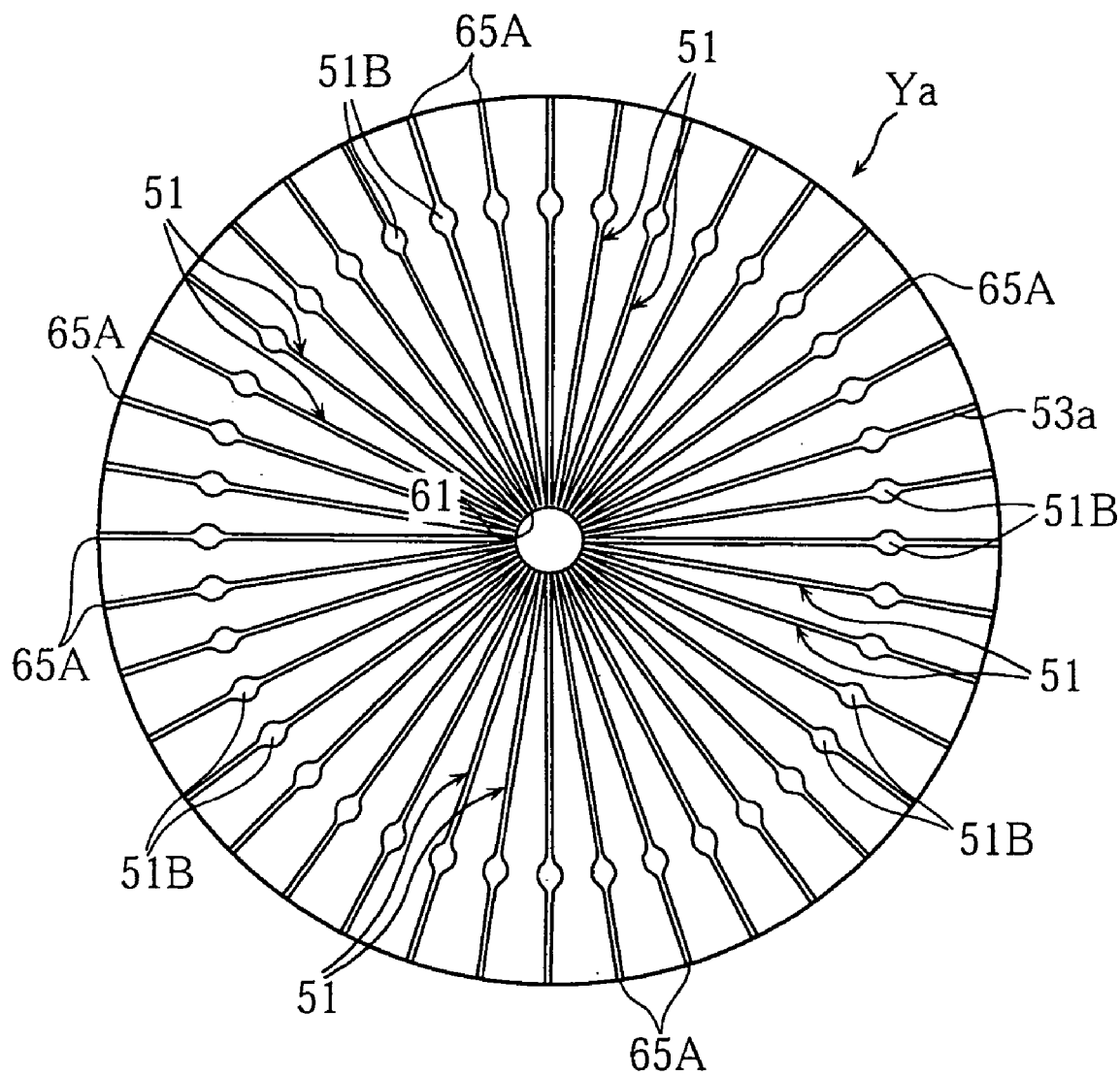
FIG. 11 is a typical plane view for explaining a microdevice according to the second embodiment of the present invention.

FIG. 11 shows microdevice Ya according to the second embodiment of the present invention.

In this microdevice Ya, multiple channels 51 are arranged radially extending linearly from liquid inlet 61 in the middle towards the outer edge, and reaction sites 51B are arranged on the same circle. In these respects it is the same as the microdevice Y explained previously (see FIG. 6). However, microdevice Ya differs from the microdevice Y explained previously (see FIG. 6) in that channels 51 communicate individually with exhaust holes 65A, with branching channels 53 and common channel 64 (see FIG. 6) omitted.

In this configuration, sample liquid introduced into channels 51 from liquid inlet 61 does not stop before reaction sites 51B but proceeds towards exhaust holes 65A by capillary action. In microdevice Ya, because liquid inlet 61 is positioned in the middle and reaction sites 51B are arranged on the same circle, the distance between liquid inlet 61 and each reaction site 51B is roughly the same. In this way, the time taken for sample liquid to reach each reaction site 51B is roughly standardized. As a result, because it is possible to standardize the reaction initiation timing and reaction times for all reaction sites 51B, analysis can be performed with great precision in the microdevice Ya as well.

Figure 12:
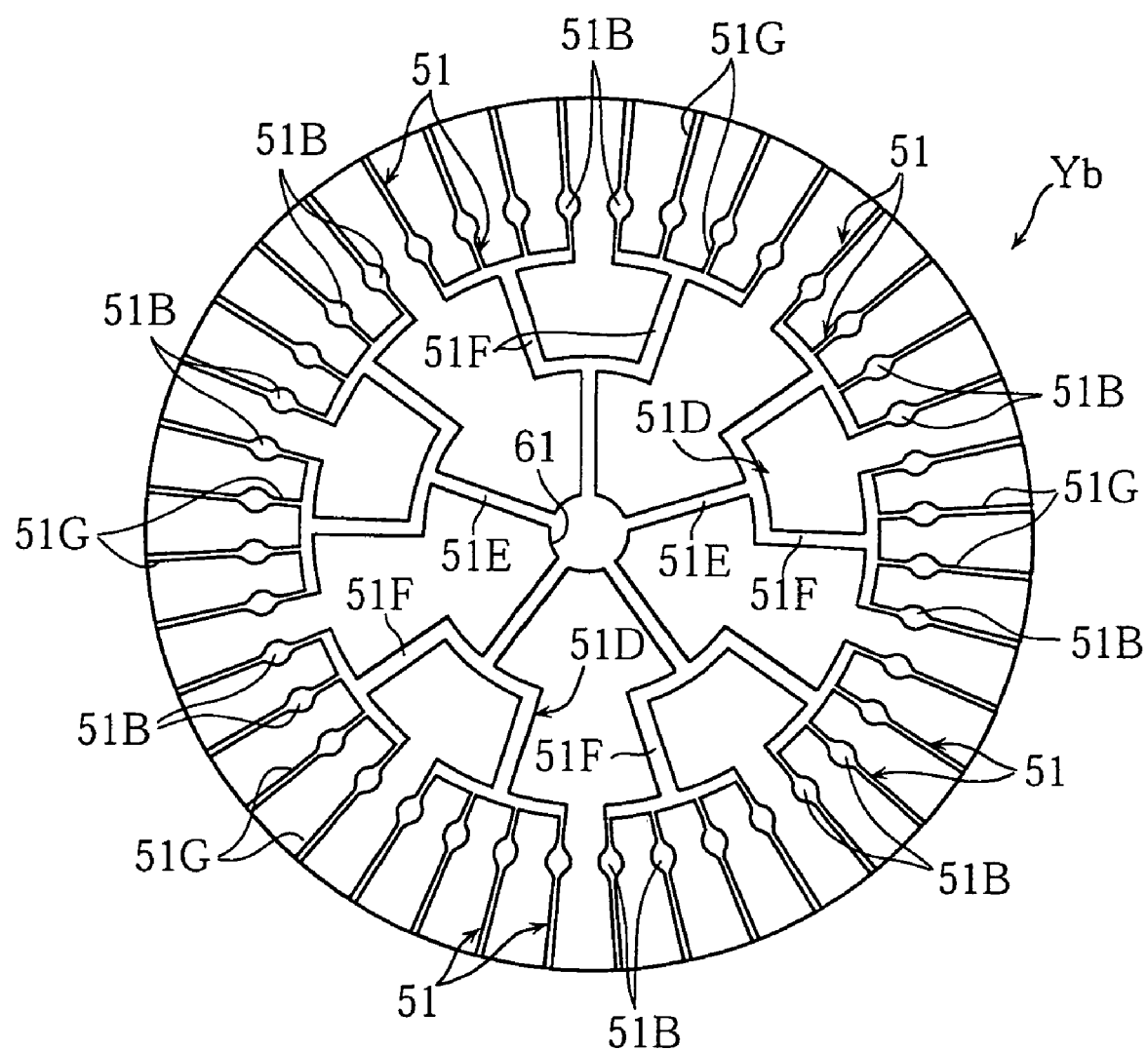
FIG. 12 is a typical plane view for explaining a microdevice according to the third embodiment of the present invention.
Figure 13A:
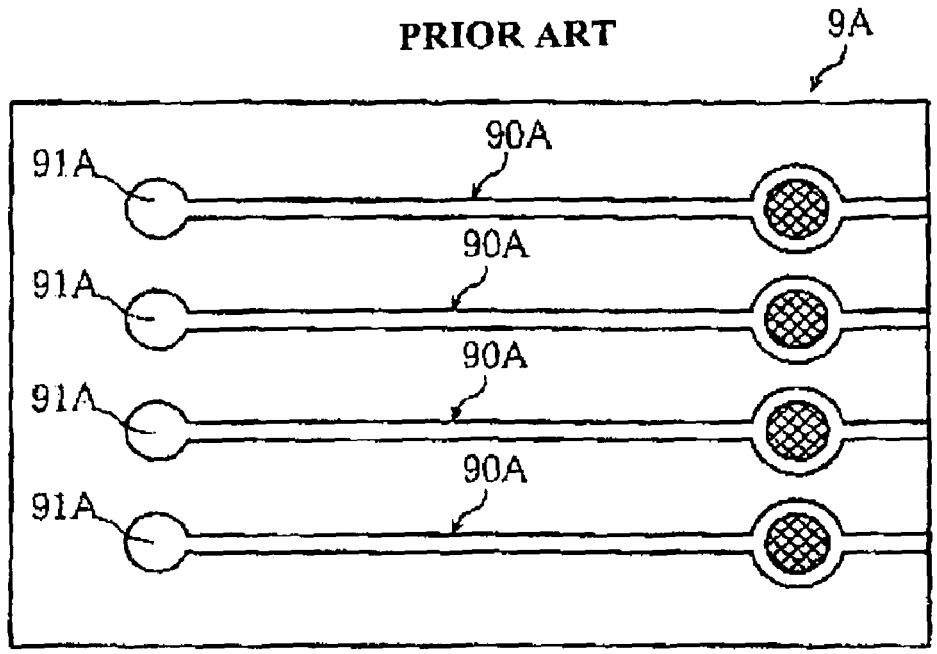
FIGS. 13A and 13B are typical plane views for explaining conventional analyzing tools
Figure 13B:
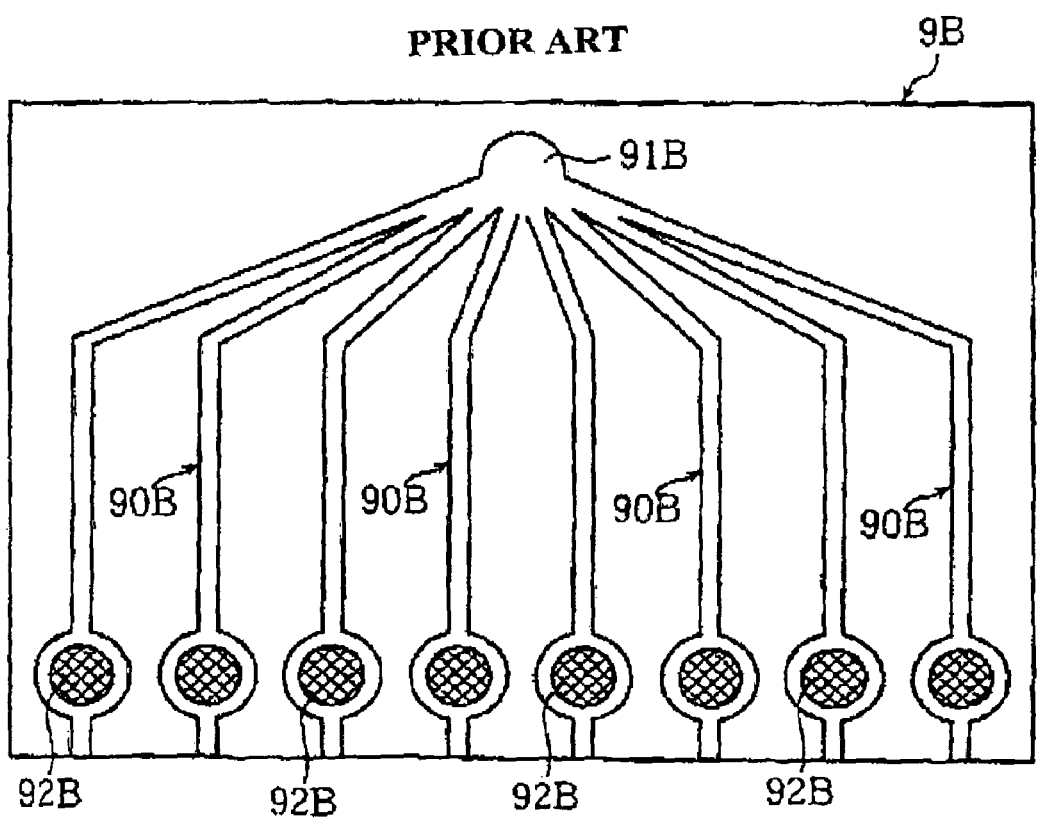

FIG. 12 shows microdevice Yb according to the third embodiment of the present invention.

This microdevice Yb is similar to the microdevice Ya (see FIG. 11) explained above in that multiple reaction sites 51B are arranged on the same circumference on the outer peripheral portion of microdevice Yb. Microdevice Yb differs from the microdevice Ya (see FIG. 11) explained above in that multiple channels 51 are grouped as multiple collective channels 51D. Each collective channel 51D has common parts 51E and 51F and individual parts 51G which include reaction sites 51B. In each collective channel 51D, common parts 51E and 51F are common to channels 51 which make up this collective channel 51D.

In this configuration, sample liquid can be supplied all at once to multiple channels 51, and moreover if the number of individual parts 51G which are the final branches (and include reaction sites 51B) is small the length of channels 51 or in other words the distance between liquid inlet 61 and reaction sites 51B can be made uniform.

In each embodiment the explanation used a microdevice formed in disk shape as an example, but the microdevice can be in another form such as a rectangle in plane view. Moreover, the technological concept of the present invention is not limited to microdevices constructed to analyze small amounts of sample liquid by optical means, but can be applied to analyzing tools which perform analyses on larger amounts of sample liquid than microdevices, or to analyzing tools configured to perform analyses by other techniques such as electrochemical techniques.

The invention claimed is:

1. An analyzing tool comprising:
   a substrate;
   a cover joined to the substrate;
   a liquid inlet formed in the cover and provided at a central portion;
   a plurality of individual channels formed in the substrate and communicating with the liquid inlet for moving a sample liquid introduced through the liquid inlet by capillary action from the central portion toward a peripheral portion of the tool;
   a common channel formed in the substrate, provided at the peripheral portion of the tool and communicating with the plurality of individual channels;
   a plurality of first gas exhaust holes formed in the cover;
   a plurality of first seals provided on the cover for closing the first gas exhaust holes, respectively, the first seals being breakable;
   a second gas exhaust hole formed in the cover; and
   a second seal provided on the cover for closing the second gas exhaust hole, the second seal being breakable;
   wherein each individual channel includes a reaction site and a branch offset from the reaction site toward the liquid inlet, the branch communicating with a corresponding one of the plurality of first gas exhaust holes, and wherein the common channel communicates with the second gas exhaust hole.

2. An analyzing tool according to claim 1, wherein each of the individual channels extends linearly from the central portion toward the peripheral portion.

3. An analyzing tool according to claim 1, wherein the plurality of individual channels are arranged radially.

4. An analyzing tool according to claim 1, wherein the reaction sites of the individual channels are arranged on a common circle.

5. An analyzing tool according to claim 4, which has a disk configuration.

6. An analyzing tool according to claim 1, further comprising reagent parts for reacting with a sample liquid, the reagent parts being provided at ones of the reaction sites of the individual channels and containing reagents different from each other.

7. An analyzing tool according to claim 1, wherein each of the individual channels has a main cross section which has a width of 10-500 μm and a depth of 5-500 μm, the depth/width ratio being $\geq 0.5$.

8. An analyzing apparatus for performing analysis of a sample liquid using an analyzing tool in accordance with claim 1,
   the analyzing apparatus comprising:
   rotating means for rotating the analyzing tool;
   a first opening-forming element for simultaneously breaking the first seals at the first gas exhaust holes; and
   a second opening-forming element for breaking the second seal at the second gas exhaust hole.

9. An analyzing apparatus according to claim 8, further comprising a fixed light source and a light detector, the light source emitting light for irradiating each reaction site in the analyzing tool, the light detector detecting light response from said each reaction site.

10. An analyzing apparatus according to claim 9, wherein the reaction sites of the individual channels are positioned at equal intervals from each other, the rotating means causing the analyzing tool to rotate intermittently at angles corresponding to the equal intervals.

* * * * *